(12) United States Patent
Russo et al.

(10) Patent No.: US 8,969,304 B2
(45) Date of Patent: Mar. 3, 2015

(54) COMPOSITIONS AND METHODS FOR THE PREVENTION OF CANCER IN HIGH RISK PATIENTS

(75) Inventors: Jose Russo, Rydal, PA (US); Irma H. Russo, Rydal, PA (US)

(73) Assignee: The Institute for Cancer Research, Philadelphia, PA (US)

( * ) Notice: Subject to any disclaimer, the term of this patent is extended or adjusted under 35 U.S.C. 154(b) by 0 days.

(21) Appl. No.: 13/640,061

(22) PCT Filed: Apr. 8, 2011

(86) PCT No.: PCT/US2011/031739
§ 371 (c)(1),
(2), (4) Date: Nov. 9, 2012

(87) PCT Pub. No.: WO2011/127380
PCT Pub. Date: Oct. 13, 2011

(65) Prior Publication Data
US 2013/0064882 A1      Mar. 14, 2013

Related U.S. Application Data

(60) Provisional application No. 61/322,666, filed on Apr. 9, 2010.

(51) Int. Cl.
*A61K 38/00* (2006.01)
*A61K 38/04* (2006.01)

(52) U.S. Cl.
CPC ........ *A61K 38/04* (2013.01); *A61K 38/00* (2013.01)
USPC ...................................................... 514/19.4

(58) Field of Classification Search
None
See application file for complete search history.

(56) References Cited

U.S. PATENT DOCUMENTS 6,635,740 B1 * 10/2003 Enright et al. .............. 530/324

OTHER PUBLICATIONS

Skolnick et al. (Trends in Biotech., 18(1):34-39, 2000).*
Freshney (Culture of Animal Cells, A Manual of Basic Technique, Alan R. Liss, Inc., 1983, New York, p4).*
Dermer (Bio/Technology, 1994, 12:320).*
Gura (Science, 1997, 278:1041-1042).*
Jain (Sci. Am., 1994, 271:58-65).*
Ezzell (J. NIH Res. 1995 7:46).*
Spitler (Cancer Biotherapy, 1995, 10:1-3).*
Boon (Adv. Can. Res. 1992 58:177-210).*
Johnson et al, Cancer Treatment Reviews, vol. 2 p. 1 (1975).*
Burgess et al, Journal of Cell Biology vol. 111 Nov. 1990 2129-2138.*
Lazar et al Molecular and Cellular Biology Mar 1988 vol. 8 No. 3 1247-1252).*
Schwartz et al, Proc Natl Acad Sci USA vol. 84:6408-6411 (1987).*
Lin et al Biochemistry USA vol. 14:1559-1563 (1975).*
Janssens, Jaak Ph., et al. "Human chorionic gonadotropin (hCG) and prevention of breast cancer." Molecular and Cellular Endocrinology. 2007; (269): 93-98.
Russo, Jose, et al. "Toward a Psychological Approach to Breast Cancer Prevention". American Association for Cancer Research. Jun. 1994. (3): 353-36.
Alvarado, Maria V., et al. "Immunolocalization of Inhibin in the Mammary Gland of Rats Treated with hCG." The Journal of Histochemistry and Cytochemistry. 1993; vol. 41, (1): 29-34.
Meduri, Geri, Ph.D, et al. "Luteinizing Hormone Receptor Status and Clinical, Pathological, and Prognostic Features in Patients with Breast Carcinomas." American Cancer Society Apr. 2003 vol. 97:(7):1810-1816.
Morbeck, Dean E., et al. "A receptor binding site identified in the region 81-95 of the β-subunit of human luteinizing hormone (LH) and chorionic gonadotropin (hCG)." Molecular and Cellular Endocrinology; Aug. 1993. 97: 173-181.
Rao, Ch. V., Ph. D. "Does Full-Term Pregnancy at a Young Age Protect Women Against Breast Cancer Through hCG?" The American College or Obstetricians and Gynecologists. Nov. 2000. vol. 96: (5): 783-786.
Russo, Jose, et al. "Breast Differentiation and Its Implication in Cancer Prevention." American Association for Cancer Research. Jan. 2005; vol. 11: 931s-936s.
Russo, Irma H., et al. "Hormonal Approach to Breast Cancer Prevention." Journal of Cellular Biochemistry Supplement. 2000; 34:1-6.
Kocdor, Hilal, et al. Human chorionic gonadtropin (hCG) prevents the transformed phenotypes induced by 17 β-estradiol in human breast epithelial cells. Cell Biology International. 2009; 33:1135-1143.
Russo, Irma H., et al. "Use of human chorionic gonadotropin in the prevention of breast cancer." Women's Health. 2008; 4(1): 1-5.

\* cited by examiner

*Primary Examiner* — Sheela J Huff
(74) *Attorney, Agent, or Firm* — Robert C. Netter, Jr.; Kathleen D. Rigaut; Dann, Dorfman, Herrell & Skillman

(57) ABSTRACT

This relates to the prevention of cancer initiation. More specifically, the invention provides compositions and methods useful for altering the genetic signature in breast tissue, said alteration being correlated with a reduced risk for the development of breast cancer.

16 Claims, 8 Drawing Sheets

COMPOSITIONS AND METHODS FOR THE PREVENTION OF CANCER IN HIGH RISK PATIENTS

This application is a §371 application of PCT/US2011/031739 filed Apr. 8, 2011, which claims priority to U.S. Provisional Application 61/322,666 filed Apr. 9, 2010, the entire contents of each being incorporated herein by reference as though set forth in full.

FIELD OF THE INVENTION

This invention relates to the fields of medicine and oncology. More specifically, the invention provides compositions and methods of use thereof to prevent initiation and progression of cancer, particularly breast cancer, before clinical disease is evident.

BACKGROUND OF THE INVENTION

Several publications and patent documents are cited throughout this application in order to more fully describe the state of the art to which this invention pertains. The disclosure of each of these citations is incorporated by reference herein.

Breast cancer, the malignant disease most frequently diagnosed in postmenopausal Caucasian women living in Northern European countries and in America (Clarke, C. A., et al. (2006) BMC Cancer, 6:170; Botha, J. L. et al. (2003) Europ. J. Cancer, 39:1718-1729), has been recently reported to increase in incidence in women under 40 years of age. Worldwide epidemiological data have reached consensus on the fact that pregnancy before age 20, i.e., early pregnancy, multiple pregnancies, and breastfeeding protect women from developing breast cancer at post menopause (Bouchardy C et al. (2007) British Journal of Cancer, 96: 1743-1746; Brinton L A, et al., (2008) J Natl Cancer Inst 100: 1643-1648). This protective effect has been observed in most ethnic groups and in women carriers of BRCA1 or BRCA2 deleterious mutations (19, 31). However, in women, whose first pregnancy occurred after age 30 or whose breast cancer is diagnosed at or before age 40, protection is not observed. These finding indicate that age at first pregnancy and age at diagnosis are two important criteria for characterizing breast cancer into two succinct risk-categories that respond differently to early life risk factors and differ in their pathogenesis (Jernström H. et al., (1999) Lancet 354(9193):1846-1850). Diagnosis of breast cancer before age 40 is prevalent among Ashkenazi Jewish carriers of BRCA1 or BRCA2 deleterious mutations and in African American women, both groups developing basal-like triple negative tumors of similar pathological and clinical characteristics. The absence of estrogen receptor (ER), progesterone receptor (PR) and Her2 that characterizes these tumors precludes the use of anti-estrogen therapy with selective estrogen receptor modulators (SERMs), such as Tamoxifen, which has been proven to effectively reduce the recurrence of early stage ER-positive breast cancer, or aromatase inhibitors that interfere with estrogen biosynthesis. Current guidelines for risk reduction strategies that are available for unaffected carriers of BRCA1 or BRCA2 deleterious mutations include multi-modality screening and prophylactic mastectomy and oophorectomy (Fatouros, M. et al., (2008) Ann Surg Oncol. 15(1):21-33.). Unfortunately, even if performed at a young age, the specimens obtained from these carriers already exhibit developmental alterations and contain pre-invasive lesions, a clear indication that any preventive measures have to be implemented several years earlier, and before age 20, which represents the optimal period for pregnancy-induced breast cancer prevention. Given the evident limitations of currently existing strategies for breast cancer prevention, it is clear a need exists to more efficiently prevent or inhibit initiation and progression of this devastating disease.

SUMMARY OF THE INVENTION

In accordance with the present invention, specific oligopeptides have been identified and tested which are useful for activating targeted pathways for optimal induction of breast tissue differentiation and thereby prevent cancer. In one embodiment of the invention, a method of preventing the initiation of cancer in a subject at high risk therefore is disclosed. An exemplary method entails treating a patient with repeated administrations of an oligopeptide selected from the group consisting of SEQ ID NO: 1, SEQ ID NO: 2, SEQ ID NO: 3 or SEQ ID NO: 4 or variants thereof, or an acceptable salt thereof, wherein each repeated administration comprises a dose of at least 0.250 mg peptide/kg bodyweight of the subject, thus preventing the development of cancer. Cancers to be treated using the compositions and methods of the invention, include, for example, breast cancer, prostate cancer, ovarian cancer, uterine cancer, endometrial cancer, brain cancer, lymphomas, tuberous-sclerosis associated angiomyolipomas and testicular cancer. The method also entails isolating nucleic acids from breast tissue before and after treatment in order to assess the patient for an altered genetic signature which is associated with a decreased risk of breast cancer. In one embodiment of the method, SEQ ID NO: 1 is administered. In another embodiment, SEQ ID NO: 2 is administered.

Another aspect of the invention comprises a pharmaceutical composition for the prevention of cancer comprising an effective amount of SEQ ID NO: 1 or variants thereof in a pharmaceutically acceptable carrier. In one embodiment, the oligopeptide is encapsulated by a liposome. In preferred embodiments, the oligopeptide is administered orally or transdermally.

DETAILED DESCRIPTION OF THE INVENTION

We have identified a particular class of peptides that inhibit both the initiation and progression of breast cancer through their specific binding to the receptor of the glycoprotein hormones luteinizing hormone and Chorionic Gonadotropin hormone (LH/CG-R). These are ALCRRSTTDCGGPKDHPLT [C→S]; SEQ ID NO: 1) PPFC-879-81-95 peptide [Sequence: Ser-Tyr-Ala-Val-Ala-Leu-Ser-Cys-Gln-Cys-Ala-Leu-Cys-Arg-Arg (NH2) SEQ ID NO: 2], PPFC-879-1-15 peptide: [Sequence: Ser-Lys-Glu-Pro-Leu-Arg-Pro-Arg-Cys-Arg-Pro-Ile-Asn-Ala-Thr (NH2) SEQ ID NO: 3]; and PPFC-879-81-95-C88A peptide: [Sequence: Ser-Tyr-Ala-Val-Ala-Leu-Ser-Ala-Gln-Cys-Ala-Leu-Cys-Arg-Arg (NH$_2$) with a (C88A substitution) SEQ ID NO: 4. Molecular modeling has revealed those residues of the ligand which are in close contact with the receptor. The structural details of this model reveal several aspects of the functional specificity conferred by the beta chain of the hCG hormone. There is an exceptionally high charge density within the interface between receptor and hormone, and correspondingly we would expect that a significant portion of the specificity of a particular hormone for its cognate receptor will be conferred by a constellation of complementary charge interactions. These peptides can be administered in a variety of formulations, including sublingual, transdermal and long-term sustained release implants. Many interactions have been identified in the model which contribute to hormone specificity. More importantly this information provides the means to target the LH/CG-R for activation by the use of small peptides thereby mimicking hormone activation, and conferring the associated protective effects against breast cancer.

Figure 1:
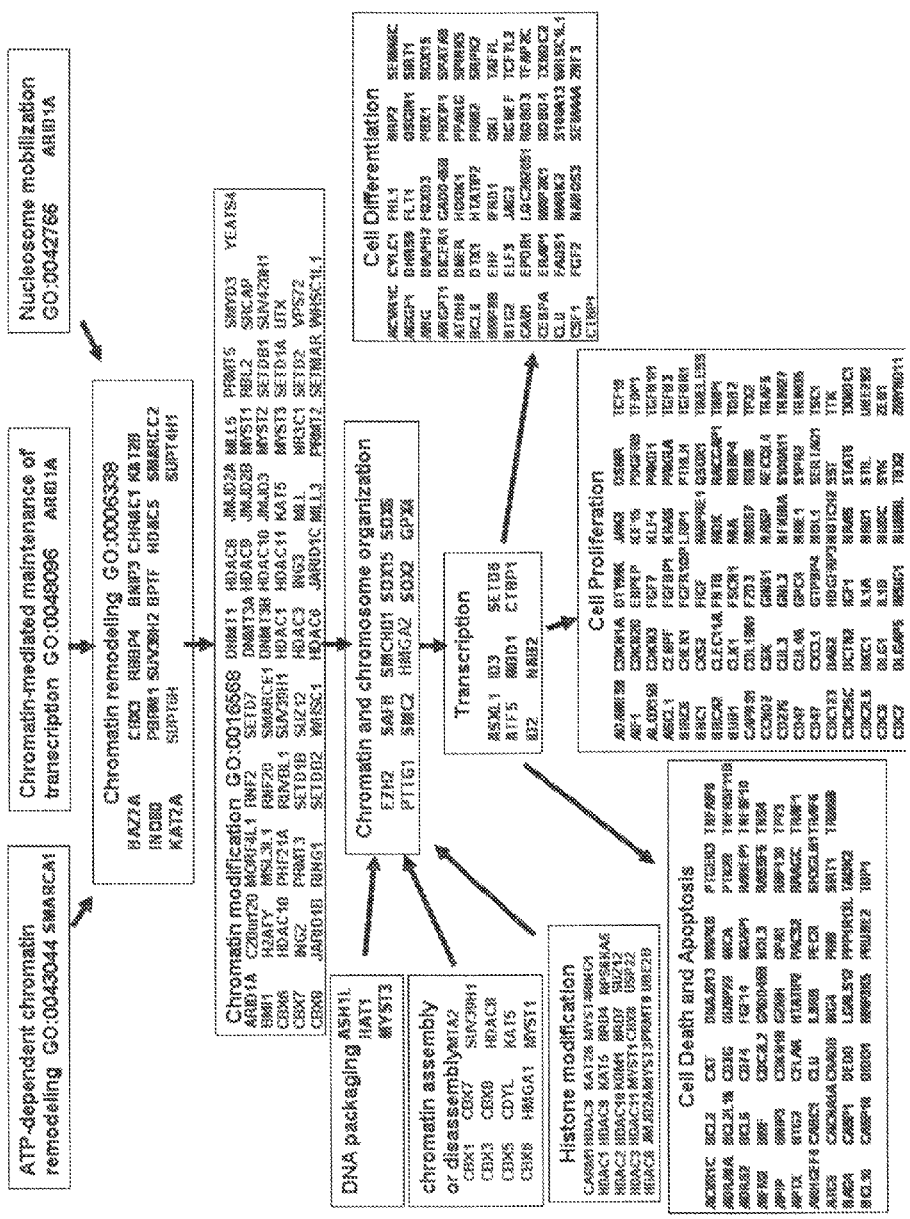
FIG. 1: Path of chromatin remodeling in the parous breast shows activation (≥2-fold, red) of genes controlling cell differentiation and cell death and apoptosis. Genes predominantly down-regulated (≥2-fold, green) are those associated with control of cell proliferation.

The lifetime decrease in breast cancer risk that occurs in those parous women whose first pregnancy was completed before age 24 indicates that pregnancy has successfully induced complete terminal differentiation, permanently modifying the genomic characteristics of the breast epithelium, thus creating a "genomic signature" of pregnancy The fact that an early first full term pregnancy does not confer protection to all women suggests that such a "genomic signature" might be defective or absent in those early parous women that develop cancer, who are predominantly represented by women belonging to high-risk groups, such as carriers of BRCA1 or BRCA2 deleterious mutations, or having a family history of breast cancer. In order to identify those genes whose expression may be affected by pregnancy and that can be proven to be functionally relevant in protecting the breast from developing cancer, we obtained breast biopsies of histologically normal tissues from postmenopausal parous women, 18 free of breast pathology (control) and 41 breast cancer patients (cases). Using laser capture microdissection (LCM), we separately collected the epithelium and the stroma of Lob 1; the RNA of each compartment and each sample was isolated, amplified using PCR methodology, and hybridized to cDNA glass-microarrays containing 40,000 genes (Russo, J. et al., (2008) Cancer Epidemiol. Biomarkers and Prevention, 17(1): 51-66). This analysis allowed us to identify 126 genes that were up-regulated and 103 down-regulated in the breast epithelium of the control group. Gene categories related to cell death and apoptosis, cell differentiation, DNA packaging, DNA repair, response to exogenous agents and transcription regulation were overrepresented among the upregulated genes. We further validated these findings in a second set of breast biopsies obtained from 20 nulliparous and 40 parous postmenopausal women free of mammary pathology. In this validation studies using Affymetrix platform we found that the categories of chromatin remodeling, chromatin modification and chromatin and chromosome organization were evenly represented as shown in FIG. 1, providing the genomic signature imprinted by pregnancy. Having this signature in hand is useful for demonstrating the chromatin remodeling achieved using the compositions and methods of the invention.

In our preclinical studies using the DMBA induced mammary tumor model (Russo, I. H. and Russo, J. (2000) J. Cell Biochem. Suppl. 34:1-6), we have shown that the susceptibility of the mammary gland to carcinogenesis is reverted by a full term pregnancy or a 21 day-treatment of virgin rats with r-hCG before carcinogen administration. The preventive effect of both pregnancy and hCG treatment is mediated by the induction of differentiation of the mammary gland, depression of DNA synthesis, and changes in the genomic profile of the gland (Russo, J., et al., (2005) Clinical Cancer Research 11:931s-936s). The most significantly upregulated genes by r-hCG treatment of virgin rats and by pregnancy that were validated by real time RT-PCR were CTBP1, KDM1, MLL5, and KDM6B, whereas RPS6KA3 and BMI1 were downregulated, changes similar to those detected in the parous breast (FIG. 1). Altogether, these data indicated that hCG, like pregnancy, induced permanent genomic changes or a "signature" in the mammary gland. The expression of this genomic signature was associated with the lowest susceptibility of these animals to DMBA induced carcinogenesis, establishing a direct relationship between a specific genomic signature and mammary cancer prevention.

Use of full length r-hCG has certain drawbacks clinically. These include the need for systemic administration or intramuscular injection, application site disorders that include injection site pain, bruising, soreness or redness; gastrointestinal system disorders such as abdominal pain, nausea, vomiting, diarrhea; general systemic disorders, i.e., headache, tiredness, irritability, restlessness, breast pain, and a rare reproductive system disorder, ovarian hyperstimulation syndrome (OHSS).

To avoid such limitations, we have developed small peptide molecules that can be administered more effectively to patients to reach their site of action. Small size peptides can be effectively administered orally, either on food intake, liquid or tablet form, or as a liquid sublingual application. Alternative non-invasive routes such as nasal sprays and skin patches for transcutaneous absorption can also deliver efficiently the compounds.

DEFINITIONS

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds.

According to the present invention, an isolated, or biologically pure molecule is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

The term "administer", "administering", or "administration", as used herein refers to either directly administering a synthetic peptide or pharmaceutically acceptable salt of the peptide or a composition to an animal, or administering a prodrug derivative or analog of the compound or pharmaceutically acceptable salt of the compound or composition to the animal, which can form an equivalent amount of active compound within the animal's body.

"Pharmaceutically acceptable" indicates approval by a regulatory agency of the Federal government or a state government. "Pharmaceutically acceptable" agents may be listed in the U.S. Pharmacopeia or other generally recognized pharmacopeia for use in animals, and more particularly in humans.

A "carrier" refers to, for example, a diluent, adjuvant, excipient, auxilliary agent or vehicle with which an active agent of the present invention is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The terms "percent similarity," "percent identity" and "percent homology," when referring to a particular sequence, are used as set forth in the University of Wisconsin GCG software program. Preferably, the variant peptides of the invention possess at least 90% identity to SEQ ID NO: 1 or 2, or more preferably 95% identity to these reference sequences.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of these ligand sequences, e.g., the ability to activate its cognate receptor.

Chemotherapeutic agents are compounds that exhibit anticancer activity and/or are detrimental to a cell (e.g., a toxin). Suitable chemotherapeutic agents include, but are not limited to: toxins (e.g., saporin, ricin, abrin, ethidium bromide, diptheria toxin, *Pseudomonas exotoxin*, and others listed above); alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, vinblastine, and paclitaxel (Taxol)); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). In a particular embodiment, the chemotherapeutic agent is selected from the group consisting of: placitaxel (Taxol®), cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives. In cases where the peptides of the invention are utilized in patients having existing tumors, administration of the peptides can be combined with administration of one or more of the anti-cancer agents described above.

"Variants", "mutants" and "derivatives" of particular oligopeptide sequences of refer to sequences that are closely related to a particular sequence but which may possess, either naturally or by design, changes in sequence or structure. By closely related, it is meant that at least about 75%, but often, more than 90%, of the amino acids of the sequence match over the defined length of the sequence referred to using a specific SEQ ID NO. Changes or differences may be specifically designed and introduced into the sequence for specific purposes, such as to increase receptor binding specificity or affinity, to increase peptide stability, etc. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence. Such variants may also include at least one, two, three, four or five additional amino acids at either one or both of the carboxy or amino terminus of the sequence, provided that such variants also exhibit the ability to alter the genetic signature of breast tissue.

The term "animal" as used herein includes, without limitation, a human, mouse, rat, guinea pig, dog, cat, horse, cow, pig, monkey, chimpanzee, baboon, or rhesus. In one embodiment, the animal is a mammal. In another embodiment, the animal is a human.

The term "vector" relates to a single or double stranded circular nucleic acid molecule that can be infected, transfected or transformed into cells and replicate independently or within the host cell genome. Such vectors are useful for producing large amounts of the anti-cancer oligopeptides described herein. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the neuroblastoma specific marker nucleic acid molecule such that the latter is transcribed into mRNA. Host cell machinery then translates mRNA into a polypeptide. Those skilled in the art will recognize that a nucleic acid vector can contain nucleic acid elements other than the promoter element and the oligopeptide of the invention. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus, that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term cancer as used herein refers to aberrant hyperproliferative disease associated with malignancy. Cancers contemplated for treatment herein include, for example, breast cancer, prostate cancer, brain cancer, uterine cancer, ovarian cancer, endometrial cancer, cancers of the hematopoietic system, testicular cancer, lymphomas and tuberoussclerosis associated angiomyolipomas.

"Sample" or "patient sample" or "biological sample" generally refers to a sample which may be tested for a particular molecule, preferably a breast cancer marker molecule, such as a marker described herein below. Samples may include but are not limited to cells, body fluids, including blood, serum, plasma, nipple aspirates, needle biopsies, saliva, tears, pleural fluid and the like.

Pharmaceuticals and Peptide Therapies

The elucidation of the role played by early pregnancy and its protective effect against the development of breast cancer facilitates the development of pharmaceutical compositions useful for the prevention of breast cancer. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, transdermal, intraperitoneal routes.

The oligopeptides of the invention are to be given to an individual in a "prophylactically effective amount" or a "therapeutically effective amount" (as the case may be, although prophylaxis may be considered therapy), this being sufficient to show benefit to the individual.

Having the sequence information for these biologically active peptides facilitates the rational design of designer peptides that exhibit greater specificity and efficacy against the hCG receptor. Small peptide molecules corresponding to these regions may be used to advantage in the design of therapeutic agents which effectively down modulate the initiation of breast cancer.

Molecular modeling should facilitate the identification of specific organic molecules with capacity to bind to the active site of the LH/CG-R based on conformation or key amino acid residues required for function. A combinatorial chemistry approach will be used to identify molecules with greatest activity and then iterations of these molecules will be developed for further cycles of screening.

The polypeptides or fragments employed in drug screening assays may either be free in solution, affixed to a solid support or within a cell. Methods for screening for anti cancer functions in breast cancer cells are provided herein. Such cells, either in viable or fixed form, can be used for standard binding assays. One may determine, for example, formation of complexes between the polypeptide or fragment and the agent being tested, or examine the degree to which the formation or a function of a complex between the polypeptide or fragment and a known substrate is interfered with by the agent being tested.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21.

Thus, one may design drugs which have, e.g., improved polypeptide activity or stability or which act as inhibitors, agonists, antagonists, etc. of polypeptide activity. By virtue of the availability of nucleic acid sequences encoding the oligopeptides described herein, sufficient amounts of the encoded polypeptide may be made available to perform such analytical studies as x-ray crystallography. In addition, the knowledge of the protein sequence provided herein will guide those employing computer modeling techniques in place of, or in addition to x-ray crystallography.

Pharmaceutical formulations for use in the invention can include vesicles encapsulating the oligopeptides, such as a liposome [see Langer, Science 249:1527-1533 (1990); Treat et al., in Liposomes in the Therapy of Infectious Disease and Cancer, Lopez-Berestein and Fidler (eds.), Liss: New York, pp. 317-327, see generally, ibid] Preferably, administration of liposomes containing the agents of the invention is parenteral, e.g., via intravenous injection, but also may include, without limitation, intra-arteriole, intramuscular, intradermal, subcutaneous, intraperitoneal, intraventricular, and intracranial administration, or by injection into the tissues being treated.

In yet another embodiment, a pharmaceutical composition of the present invention can be delivered in a controlled release system, such as using an intravenous infusion, an implantable osmotic pump, a transdermal patch, liposomes, or other modes of administration. In a particular embodiment, a pump may be used [see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)]. In another embodiment, polymeric materials can be used [see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. 23:61 (1983); see also Levy et al., Science 228: 190 (1985); During et al., Ann. Neurol. 25:351 (1989); Howard et al., J. Neurosurg. 71:105 (1989)]. In yet another embodiment, a controlled release system can be placed in proximity of the target tissues of the patient, thus requiring only a fraction of the systemic dose [see, e.g., Goodson, in Medical Applications of Controlled Release, supra, vol. 2, pp. 115-138 (1984)]. Other controlled release systems are discussed in the review by Langer [Science 249:1527-1533 (1990)].

Clinical Protocol

Forty six premenopausal nulliparous BRCA½ carrier women will be entered in the study. After obtaining a baseline breast biopsy by FNA or CNB they will receive 250 µg of SEQ ID NO: 1, 2, 3, 4 or full-length r-hCG 3 times per week for at least 3 months. Screening for the study will include a blood hematology, biochemistry (including serum tumor marker), endocrinology and urinalysis, and breast and ovarian size assessment by ultrasound. At the end of the 3 month treatment and at 6 months post-treatment, there will be a re-evaluation of the genomic profile of breast cells using the same diagnostic procedure(s). The treatment will be considered effective if normal tissue biopsies after 3 months of treatment and 6 months post a peptide treatment will be more effective than r-hCG in inducing in the breast a genomic signature of protection comprised of a distinctive set of markers indicating that chromatin remodeling had occurred, such as the expression of genes associated with cell differentiation, cell proliferation, programmed cell death, DNA repair damage, and specific non coding sequences and microRNAs, as well as a complete epigenetic make up to provide an accurate and definitive profile of the biochemical interactions which give rise to prevention.

Kits and Articles of Manufacture

The aforementioned cancer preventing oligopeptides can be incorporated into a kit which may contain in addition to a therapeutically effective amount of the oligopeptide, a pharmaceutically acceptable carrier, a physiologically acceptable carrier, a transdermal patch, a controlled release pump, instructions for use, a container, a vessel for administration, or any combination thereof.

The following examples are provided to illustrate certain embodiments of the invention. They are not intended to limit the invention in any way.

Example I

Compositions for Mimicking Pregnancy to Attain a Differentiation Genetic Signature Associated with a Reduced Risk for the Development of Future Breast Cancer In our preclinical studies using the DMBA induced mammary tumor model (Russo et al., supra) we have shown that the susceptibility of the mammary gland to carcinogenesis is reverted by a full term pregnancy or a 21 day-treatment of virgin rats with r-hCG before carcinogen administration. The preventive effect of both pregnancy and hCG treatment is mediated by the induction of differentiation of the mammary gland, depression of DNA synthesis, and changes in the genomic profile of the gland. The most significantly upregulated genes by r-hCG treatment of virgin rats and by pregnancy that were validated by real time RT-PCR were CTBP1, KDM1, MLL5, and KDM6B, whereas RPS6KA3 and BMI1 were downregulated, changes similar to those detected in the parous breast (FIG. 1). Altogether, these data indicated that hCG, like pregnancy, induced permanent genomic changes or a "signature" in the mammary gland. The expression of this genomic signature was associated with the lowest susceptibility of these animals to DMBA induced carcinogenesis, establishing a direct relationship between a specific genomic signature and mammary cancer prevention.

Based on our preclinical studies and those described above we have initiated an NCI funded pilot study. Eligible women are asymptomatic nulliparous BRCA1 carriers (20 to 40 years of age) that receive on alternate days three sc injections of 250 µg of r-hCG (Ovidrel, Serono) for three months. The primary end point of the study is the measurement of gene expression in breast epithelial cells obtained by CNB at baseline (time 0), at the end of treatment with r-hCG at 12 weeks (time 1) and at 39 weeks from baseline (time 3). Our preliminary findings that in two of the volunteers that have already finished the treatment with r-hCG the genomic signature of the breast tissue exhibits a shift of the same group of genes detected in parous women (FIG. 1), are encouraging.

Effect of r-hCG and Synthetic Peptides on in Vitro Transformation of Human Breast Epithelial Cells.

Figure 2:
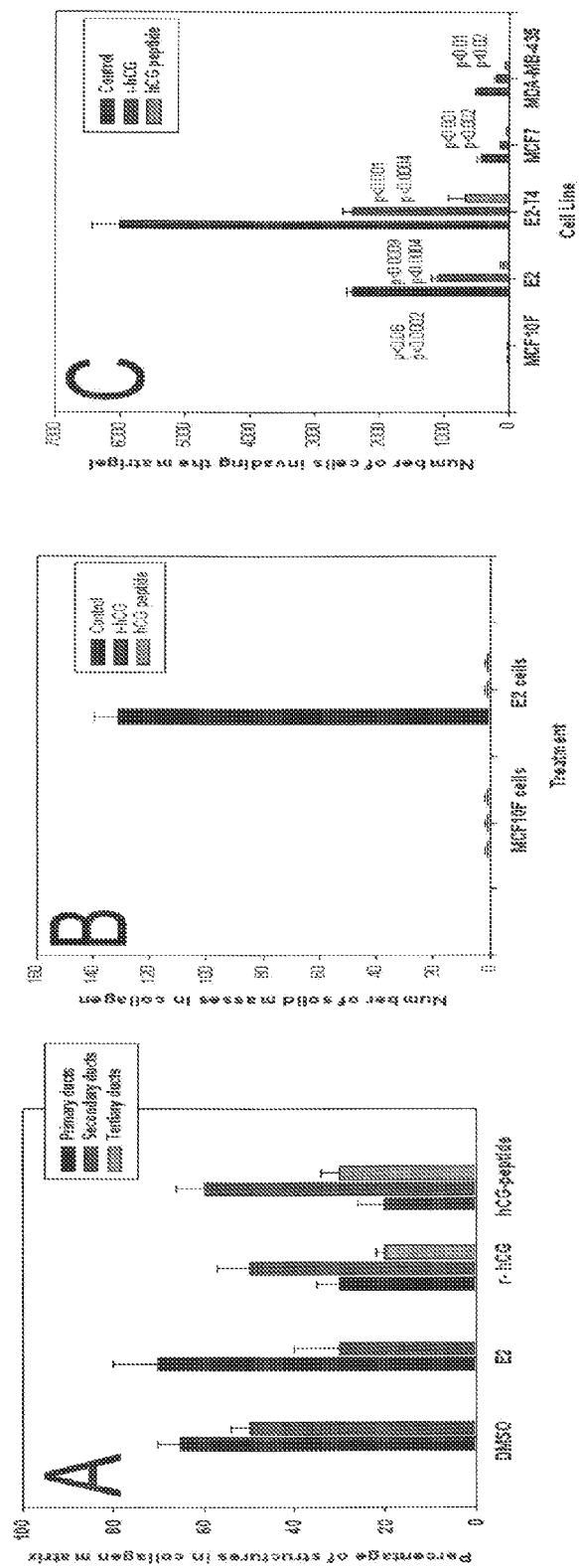
FIG. 2: (A) Effect of 17b-estradiol ($E_2$), r-hCG and PPFC-879-81-95 peptide on formation of primary, secondary, and tertiary ducts by MCF10F cells grown in a collagen matrix. DMSO served as control. Ordinate, percentage of structures. (B) Effect of r-hCG and hCG peptide on colony formation. Only DMSO-treated (control) E2-cells formed solid masses. (C) Effect of r-hCG and hCG peptide on the invasive index of MCF10F, $E_2$-transformed, $E_2$T4, MCF-7 and MDA-MB-435 cells. Ordinate, number of cells traversing a matrigel membrane.

We have demonstrated that the human breast epithelial cells (HBEC) MCF-10F reproduce the normal processes of ductulogenesis and branching, mimicking the architectural pattern of the normal breast in vivo when seeded in a 3D collagen matrix. The cells grow along hollow branches forming ductules lined by a monolayer of epithelial cells. These normal-appearing ductules become disarrayed when the cells are treated with chemical carcinogens (Russo, J., et al., (1995) In: Hormonal Carcinogenesis II (Li, et al., eds.) Springer Verlag, Berlin, pp 120-131.) or with $E_2$ (Russo, J., et al., (2002) Eur. J. Cancer, 38 Suppl. 6: S31-32), forming instead spherical structures with a multilayered epithelium that exhibits marked atypia, similar to that observed in atypical hyperplasia and in situ carcinomas reported in primary breast lesions. Treatment of $E_2$-transformed MCF-10F cells with 2.5 mcg/ml r-hCG resulted in a significant decrease in the number of solid masses in comparison with the controls. The hormonal treatment also increased the number of secondary and tertiary branching in the ductular structures, a phenomenon that characterizes the differentiating properties of r-hCG (Kocdor, H. et al., (2009) Cell Biology International 33(11): 1135-43). For these studies, we designed oligopeptides of the hCG beta subunit and had them synthesized by AAPPTec, LLC, Louisville, Ky. We selected a 15 aa peptide with a sequence "N"-SYAVALSCQCALCRR-"C" (SEQ ID NO: 2) that encompasses aa 81-95 and was designated PPFC-879-81-95. It was tested in the in vitro system described above; its addition to the culture medium increased the branching pattern of MCF-10F cells by increasing the number of secondary and tertiary ducts (FIG. 2A). It also abrogated more efficiently than r-hCG the formation of solid masses in collagen (FIG. 2B) and inhibited invasiveness in MCF-10F cells, in their derived $E_2$-transformed and tumor derived $E_2T4$ cells, and in the breast cancer cell lines MCF-7 and MDA-MB-435 (FIG. 2C).

Genomic analysis of r-hCG and peptide-treated cells revealed that SEQ ID NO: 2 induced activation or downregulation of the same clusters of genes that were modified by either parity or r-hCG treatment (FIG. 1). Interestingly, BMI1, a known regulator of stem cell self-renewal, is modulated by miR-200c, which inhibits the clonal expansion of breast cancer cells and suppresses the growth of embryonal carcinoma cells in vitro. The down-regulation of BMI1 supports the concept that the preventive effect of hCG results from the shifting of the stem cell 1 to stem cell 2 (Russo, J., et al., (2006) Front Biosci., 11:151-172). This is only one example of identification of the molecular determinants of hormone specificity which provide the means to target the CG/LH-R for activation thereby conferring the protective effects against breast cancer. Further research has revealed that a peptide encompassing hCG residues 91 to 110 (AL-CRRSTTDCGGPKDHPLT[C→S]) (SEQ ID NO: 1) would bind the hCG receptor with greater affinity.

Example II

Interaction of r-hCG and SEQ ID NO: 2 with the hCG Receptor

Figure 3:
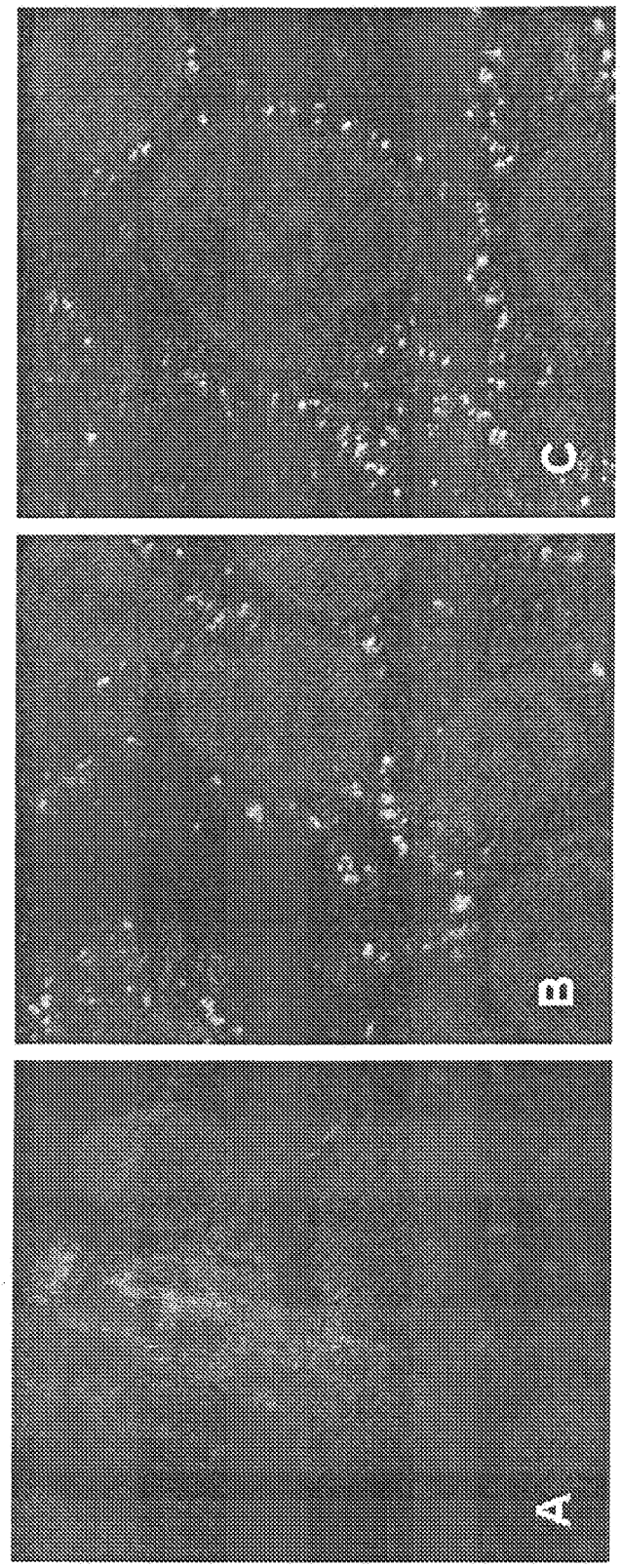
FIG. 3: Immunocytochemical detection of CG/LH-R in MCF10F cells. (A) MCF10F negative control; (B) MCF10F cells, and C, $E_2$ transformed MCF10F cells. Cells incubated with 20C3 mAb exhibited a punctated reaction along the plasma membrane Stained with goat-antimouse 488 AlexaFluor; blue stained nuclei (DAPI).
Figure 4:
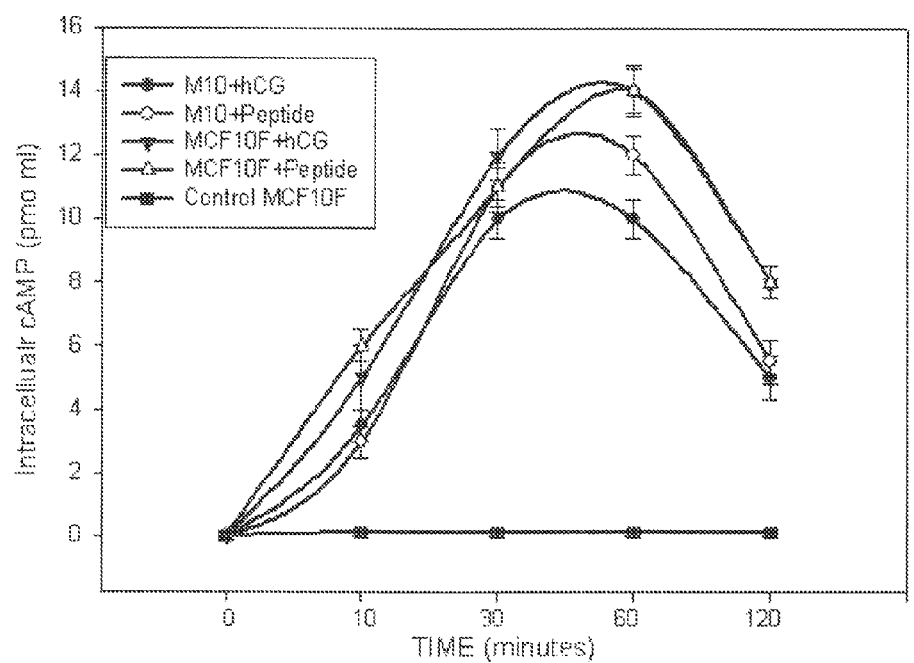
FIG. 4: Intracellular cAMP concentration in pmol/ml (ordinate) measured in acetylated MA-10 and MCF10F cells using a cAMP enzyme immunoassay kit (EIA CA201, Sigma-Aldrich, St. Louis, Mo.).

The hCG receptor is a member of the subfamily of glycoprotein hormone receptors within the superfamily of G protein-coupled receptor (GPCR). The hormone-binding domain has been localized to exons 1-7 in the extracellular (EC) domain/region of the receptor, which contains several leucine rich repeats. High-affinity binding of hCG and LH causes secondary hormone or receptor contacts to be established with regions of the EC loop/transmembrane module that initiate signal transduction. CG/LH-R coupling functions are exerted primarily through cAMP/protein kinase A-mediated events in the gonads (Zhang Y, et al., (2008) The Journal of Biological Chemistry, 283:24039-24046). For verifying the presence and functionality of the receptor in normal and transformed MCF10F cells we used the monoclonal antibody (mAb) 20C3 raised against the human LHR-transfected Chinese hamster ovary (CHO-LHR) cells, which was kindly provided by Drs. A. Funaro and F. Malavasi, from the Dept. Genetics, Biology and Biochemistry at the University of Torino, Italy. We used as positive control MA-10, a mouse Leydig tumor cell that was kindly provided by Dr. M. Ascoli from the Dept. of Pharmacology, Univ. of Iowa, Iowa City, Iowa. MCF10F and $E_2$-transformed cells exhibited a punctuate positive reaction along the plasma membrane (FIG. 3), in a distribution similar to that seen in MA-10A cells. For testing the functional capacity of hCG and the PPFC-879-81-95 peptide (SEQ ID NO: 2) MA-10 and MCF10F cells were treated with 2.5 µg r-hCG/ml or 20 µM PPFC-879-81-95 by measuring their effect on intracellular cAMP production following the manufacturer's recommended procedures (FIG. 4). Both treatments induced in MA-10 and MCF10F cells a time-dependent increase in intracellular cAMP production, indicating that the expressed human LH/hCG-R functionally couples with endogenous adenylyl cyclase.

Molecular Modeling of PPFC-879-91-110 Peptide.

We have constructed a model of hCG bound to the CG/LH-R, based on the PDB structure 1XWD (Fan Q R, et al., (2005) Nature 433(7023):269-77). The sequences of hCG and CG/LH-R were aligned to their respective templates using the program MolIDE, and side chain conformations of the protein and peptide were predicted with the program SCWRL (Canutescu, A. A., et al., (2003). Protein Sci 12, 2001-14.91-94), allowing all side chains to move in both hormone and receptor. The structural details of this model reveal several aspects of the functional specificity conferred by the beta chain of the hormone. There is an exceptionally high charge density within the interface between receptor and hormone, and correspondingly we would expect that a significant portion of the specificity of a particular hormone for its cognate receptor will be conferred by a constellation of complementary charge interactions.

Figure 5:
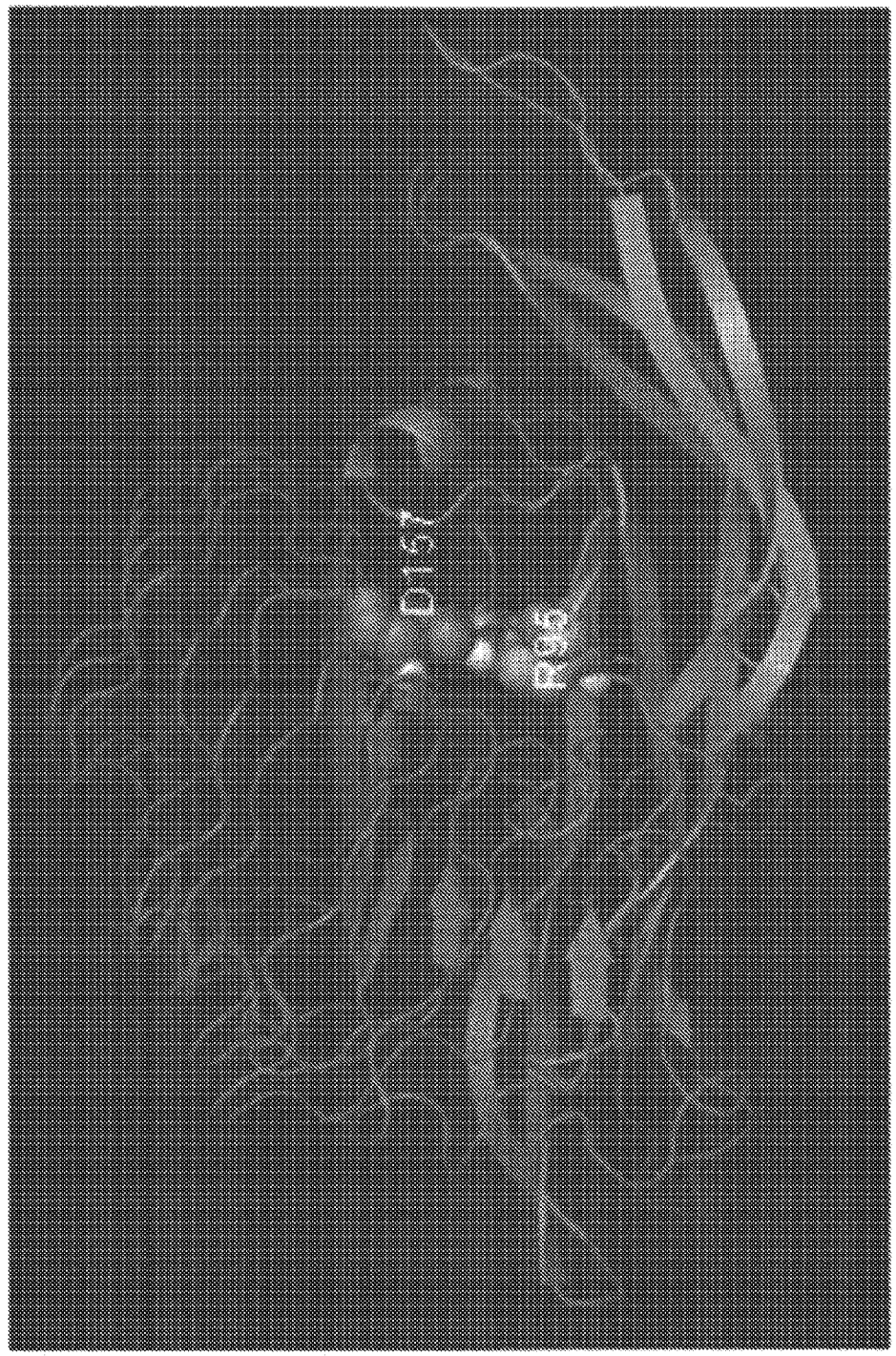
FIG. 5: Specificity determining hCG residue R95/115 making contact with CG/LH-R residue D157.

One such interaction that could contribute to specificity of hCG for its cognate receptor involves PPFC-879-91-110, a peptide encompassing residues 91 to 110 (ALCRRSTTDCG-GPKDHPLT[C->S]; SEQ ID NO: 1), which is predicted by our model to make intimate contact with the receptor at position D157 (FIG. 5).

The following materials and methods are provided to facilitate the practice of Example III.

Human Breast Epithelial Cell Treatment with Recombinant Human Chorionic Gonadotropin (rhCG) or 15 aa Peptide MCF-10F, a spontaneously immortalized human breast epithelial cell line spontaneously immortalized, estrogen receptor alpha (ERa)-negative, beta (ERb)-positive and progesterone receptor (PR)-negative, was cultured in Dulbecco's modified Eagle medium [DMEM/F-12, Gibco; Formula 90-5212 EF: containing DMEM/F12 (1:1) supplemented with L-glutamine and phenol red, with D-glucose 315 mg/L, with sodium pyruvate 55 mg/L] with 5% horse serum, 2.43 g/l sodium bicarbonate, 20 mg/l epidermal growth factor (EGF), 100 mg/l *Vibrio cholera* toxin, 10 mg/l insulin, 0.5 mg/l hydrocortisone, 1.05 mM calcium, antibiotics and antimicotic (100 units/ml penicillin, 100 mg/ml streptomycin, 0.25 mg/ml amphotericin). The cells were treated continuously with 50 IU/ml of recombinant human chorionic gonadotropin (r-hCG; Ovidrel®) or 20 µM of peptide, the most active concentration value according to Morbeck et al. (1993) Mol Cell Endocrinol 97(1-2):173-81, with the following primary structure, SFP VAL SCR CGP CRR-$NH_2$, (SEQ ID NO: 5; purchased from San Francisco Scientific) during 15 days. Another group was left untreated and maintained in the regular culture media (regular media group). Untreated cells were used as control group and in all groups, the culture medium was replaced daily. During treatment phase, the cells were incubated at 37° C. In the time points 0, 1, 2, 4, 6, 8, 10 and 15 days the cells were harvested for RNA extraction and cell count. A concentration of 50 IU/ml rhCG (r-hCG; Ovidrel®) was chosen based in previous results.

Cell Proliferation Assay

Cells were brought into suspension and seeded ($1 \times 10^4$ cells/well) onto 24-well plates or 25 cm² cell culture flask in the presence of 10% (v/v) fetal bovine serum. Cells were trypsinized and counted for 12 days. After removing the medium the cells were re-suspended in 3 ml (25 cm² flask) of 0.25% trypsin/EDTA at room temperature, and then trypan blue was added. Cell count was done in a Neubauer hemacytometer (Hausser Scientific) (24). All assays were performed at least twice and each treatment was performed in triplicate wells. Statistical significance was assessed using Student's t-test.

RNA Isolation

RNA was extracted from the cells using TRIzol Reagent (Invitrogen, Foster City, Calif.) following the manufacturer's instructions. The precipitated RNA from the aqueous phase was washed with 75% ethanol. The RNA was dried and dissolved in RNase-free water. Total RNA was then purified with Qiagen RNeasy MiniKit (Qiagen, Valencia, Calif.) and submitted to DNAse treatment. The amount and quality of the extracted RNA was assessed by spectrophotometry using NanoDrop v3.3.0 (NanoDrop Technologies Inc., Rockland, Del.) and capillary electrophoresis using Bioanalyzer 2100 (Agilent Technologies Inc., Palo Alto, Calif.) respectively.

Real Time RT-PCR Analysis

A commercially available Assay-on-Demand kit (Applied Biosystems) was used to assess gene expression of LHCGR (Hs00174885_m1), of CXCR1 (IL8RA; Hs00174146_m1), of GPR30 (GPER; Hs00173506_m1) and of 18S (Hs99999901_s1) on all samples on all samples 18S was used as housekeeping gene. All RT-PCR reactions were performed on an ABI Prism 7000 Sequence Detection System (Applied Biosystems, Foster City, Calif.) using the fluorescent Taqman methodology (TaqMan One Step RT-PCR Master Mix Reagents, Applied Biosystems, Foster City, Calif.). 100, 200 or 400 ng of total RNA (Table 1) was used for each RT-PCR reaction in a total volume of 50 µl according to the manufacturer's protocol. The thermal cycling conditions were as follow: 30 s at 48° C., 10 min at 95° C., and 40 cycles of 15 s denaturation at 95° C. and 60 s annealing at 60° C. CT values were used as end point defined as the PCR cycle number in which the fluorescence generated by the amplification crosses the threshold. Three replicate reactions per sample were run to ensure statistical significance.

For data analysis, we used the comparative CT method (also known as the 2-ΔΔCt method) (25) to calculate relative quantities (RQ) of gene expression among the samples. DataAssist™, software developed for quick analysis of TaqMan® real-time PCR (*Applied Biosystems*), was used to confirm the data calculations performed in Excel. Whenever receptor quantification exceeded 36 amplification rounds (CT), quantities were considered to be undetectable or very low and measurements were taken as invalid. Statistical significance was assessed using Student's t-test.

Example III

IL-8 Receptor CXCR1 Expressed in Human Breast Epithelial Cells is Down Regulated by Human Chorionic Gonadotropin and its Peptide 81-95

Cytokine receptors belong to the large family of G-protein coupled receptors (GPCR) that are known to be associated with tumor cell growth by contributing to increase proliferation, and their aberrant expression aggravates the ability of transformed cells to metastasize towards specific organs releasing chemoattractant compounds by regulating self renewal of cancer stem cells (CSC) (1, 2). Among the cytokines, IL-8 release is associated with inflammatory processes and carcinogenesis and its presence can be detected within the tumor microenvironment (3). Cells displaying stem cell characteristics collected from normal human mammary glands as well as from breast carcinomas were demonstrated to have a strong correlation with the cytokine IL-8 receptor (CXCR1) overexpression (4), and the cells overexpressing this receptor are highly associated to an increase in the invasive and in the metastatic potential of tumors (5). Furthermore, CXCR1 blockade has been shown to reduce the number of breast CSC both in vivo and in vitro, as well as it induced apoptosis and retarded growth and metastasis of the tumor in vivo (4). This being the case, it becomes relevant to find a compound which physiologically control the down-regulation of this receptor in order to abrogate the effects triggered by the binding of cytokines.

In addition to that, some of our previous findings show that 17-β-estradiol ($E_2$) initiates neoplastic transformation of human breast epithelial cells (HBECs) led us to clarify the relationship between normal breast epithelial cells and cancer stem cells (CSCs). HBECs MCF-10F transformed in vitro by $E_2$ express increased colony efficiency, invasiveness and tumorigenesis in SCID mice and lose ductulogenesis in collagen (6). Cancer progression is associated with gene dysregulation and chromosomal aberrations, amplifications and losses. Progressive changes occur from transformed to tumorigenic and tumor-derived cell lines in the integrin signaling pathway, inhibition of apoptosis, acquisition of tumorigenic cell surface and mesenchymal markers, like fibronectin, vimentin, and N-cadherin (CDH2) during epithelial-mesenchymal transition (EMT) (7), while epithelial markers E-cadherin (CDH1), occludin (OCLN), desmoplakin, and cytokeratins progressively decrease. The cell surface molecule $CD44^+/CD24^{/low}$ phenotype, a marker for tumor-initiating cells, is significantly increased in tumorigenic and tumor derived cell lines.

Loss of ductulogenesis in $E_2$ transformed cells in collagen is reverted by human chorionic gonadotropin (hCG) (8), a hormone that induces differentiation of the breast epithelium, inhibits cell proliferation, increases apoptosis and DNA repair capabilities of the epithelial breast tissue and it also decreases the binding of carcinogens to the mammary cell DNA (9, 10). Besides that the hormone also induces branching of MCF-10F cells, a phenotype indicative of cell differentiation suggesting that rhCG has significant potential as a chemo-preventive agent, protecting normal breast cells from becoming malignant (8).

hCG actions are mediated by a G-protein-coupled receptor (11, 12) and it has been demonstrated that both pregnancy and exogenous hCG administration protect the mammary glands not only against malignant lesions but also against tumor progression (13, 14). In order to obtain an analog molecule to hCG, two series of overlapping peptides comprising the entire sequence of hCG was tested for its ability to inhibit the binding of $^{125}$I-labeled hCG to rat ovarian membranes and the most potent inhibitor of LH/hCG binding was a peptide containing the sequence 81-95 of hCG(15). From here on, it will be referred as 15aa peptide of the hormone or only peptide. In fact, consistent with hCG function in breast tissue, hCG/LH receptor (LHGCR), a class I GPCR, has been detected in normal breast epithelial cells (16-21) and although there is some consensus in the previous finding that LHCGR is expressed at higher levels in the normal breast cells when compared to breast tumor cells, the expression of this receptor in primary tumors and in breast cancer cell lines has been a controversial issue. However the study conducted by Kuijper and colleagues (2009) (22) has shed some light on it, showing categorically that the LHCGR expression cannot be detected or is extremely low in breast cancer tissues, and in breast cancer cell lines (22). However, the grade of differentiation of the mammary epithelial cell seems to be correlated with the receptor expression (22). These findings are critical considering that it has been proposed that hCG may be useful in the prevention and/or treatment of breast carcinoma (14, 19, 23).

Since no direct association between the CXCR1 and hCG/LH membrane receptors has been found in the literature, our goal here is to assess and compare the mRNA expression of these two receptors after the in vitro treatment of normal breast epithelial cells with hCG and the peptide.

Results

Cell Proliferation Assay

Figure 6:
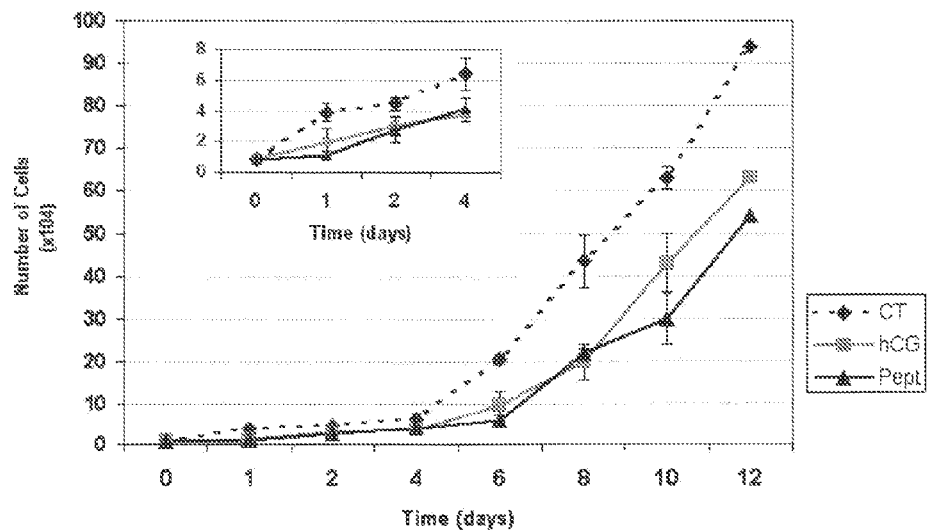
FIG. 6: Cell proliferation curve of MCF-10F cells treated with hCG or peptide. In detail the cell proliferation curve of the cells for 0 to 4 days. *, Different from Control; p<0.05 (Test t).

The quantification of viable cells clearly revealed that within 1, 2, 4, 6, 8, 10 and 12 days of hormonal treatment there were significant differences in the growth (p<0.02) between control and hCG treated cells, and between control and peptide treated cells (FIG. 6). hCG treatment caused a decrease in the number of viable cells that ranged from 33 to 69%, while the peptide evoked a similar decrease in the number of viable cells, ranging from 36 to 72% when compared to the values obtained for control. It can be seen in FIG. 6 that the curve can be divided into two distinct parts independently of which cell group is considered. The first part is comprised by days 0 to 4, and it is the result of a slow cell growth, whereas in the second one, from the fourth day on, the curve displays a higher slope typical of an exponential cell growth. Although the curve is comprised of two different parts, cell proliferation inhibition is present all along the treatment, in every time point of cell count, and in the last two time points (days 10 and 12) the peptide was a more potent cell proliferation inhibitor than hCG (p<0.02).

Real Time RT-PCR

The three genes described herein exhibited very low expression values, with detectable amplification values (CT values) close to the limit considered trustable, 36. For this reason, we ran reactions with increasing amounts of RNA (100 ng, 200 ng and 400 ng). LHCGR and CXCR1 had expected responses, in which increase of total RNA input produced lower CT values, while GPR30 had very low expression values even with higher RNA concentrations (Table 1).

TABLE 1

| | [RNA] (ng/reactionl) | CT values Mean ± SD | Minimun CT | Maximun CT |
|---|---|---|---|---|
| CXCR1 | 100 | 35 ± 0.6 | 34 | 36 |
| | 200 | 32 ± 0.4 | 31 | 33 |
| LHCGR | 100 | 36 ± 1.0 | 34 | 37 |
| | 200 | 35 ± 1.0 | 33 | 36 |
| | 400 | 34 ± 1.0 | 32 | 36 |
| GPR30 | 100 | 37 ± 0.7 | 36 | 39 |
| | 200 | 36 ± 0.7 | 35 | 38 |
| | 400 | 36 ± 0.8 | 34 | 37 |

SD, Standard Deviation

Figure 7:
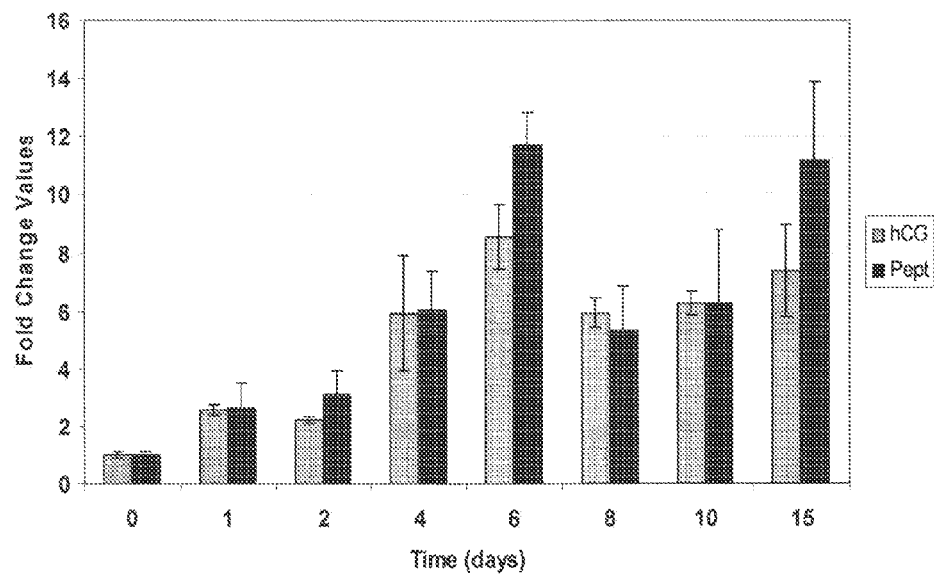
FIG. 7: Graph showing the results for LHCGR gene expressions from the real time PCR. Gene expression of MCF-10F cells treated with hCG hormone (grey bar) or treated with peptide analog of hCG (black bar).

LHCGR Expression hCG receptor gene expression was up-regulated when the breast epithelial cell line MCF-10F was treated either with hCG or the peptide. The up-regulation is observed from the first day of treatment and on. The highest values of gene expression were induced both in the middle and at the end of the treatment period. Fold change expression ranged from 2.2 to 8.6 in the hCG treated cells when compared to the control cells and from 2.6 to 11.7 in the peptide treated cells when compared to the control cells (FIG. 7). On the last day of treatment ($15^{th}$), it was observed a tendency of the peptide to induce a higher levels gene expression than hCG (p=0.06).

CXCR1 Expression

Figure 8:
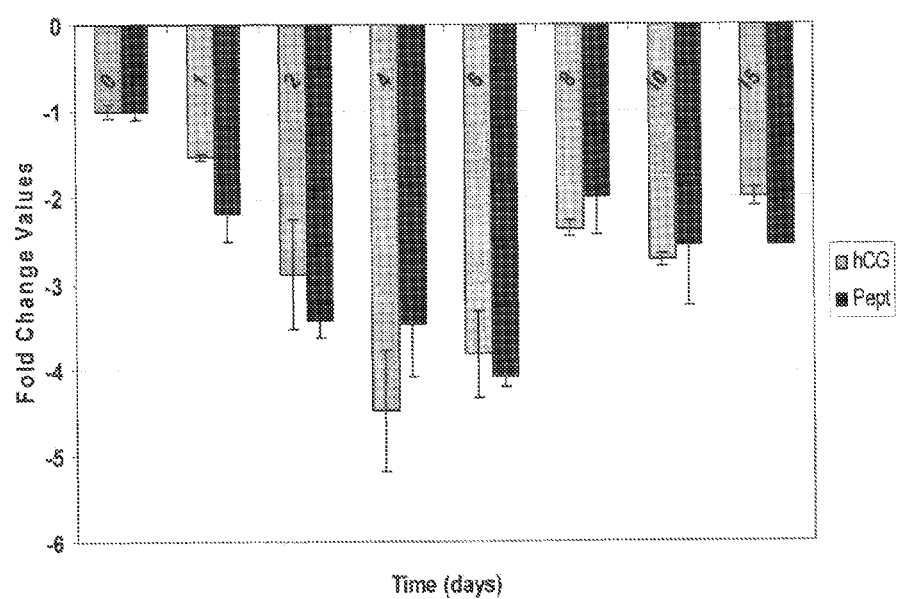
FIG. 8: Graph showing the results for CXCR1 gene expressions from the real time PCR. Gene expression of MCF-10F cells treated with hCG hormone (grey bar) or treated with peptide analog of hCG (black bar).

CXCR1 expression was down-regulated when the breast epithelial cell line MCF-10F was treated with hCG or peptide. The down-regulation was evoked all along the treatment. The lower values of expression were induced in the middle of the treatment ($4^{th}$ and $6^{th}$ days). Fold change expression ranged from 1.53 to 5.0 in the control cells when compared to the hCG treated cells and from 2.2 to 4.1 in the control cells when compared to the peptide treated cells. (FIG. 8). On the last day of treatment (15) down-regulation of the receptor was more apparent in the peptide-treated cells than in hCG treated cells (p<0.01).

GPR30 Expression

Although GPR30 receptor is similar to CXCR1 (also a class 1 and subfamily A2 of the large GPCR family with 32% of homology), untreated cells, hCG and peptide treated MCF-10F cells displayed undetectable or very low values of GPR30 mRNA expression (data not shown). Therefore, GPR30 gene expression was considered as a negative control, in order to demonstrate that the hormone did not interfere with this gene expression.

Discussion

The association between age at first full term pregnancy and breast cancer risk (26) has been reported and it has been postulated that this protective effect is mediated by the hormone hCG (13, 14). The present data provides additional evidence that hCG inhibits cell proliferation and is associated with decrease of CXCR1 transcription, a gene that mediates tumor growth and metastasis. Interestingly the 15aa peptide of the hCG hormone comprising the amino acids residues 81 to 95 of the β-subunit evoked similar effects to the ones produced by hCG when it comes to cell proliferation inhibition and expression of the membrane bound receptors LHCGR, CXCR1 and GPR30.

We confirm the data previously published by Alvarado and colleagues (1993) (27) that shows that hCG inhibits MCF-10F growth when cells are treated with doses of 50 IU. In the present work, we show that a peptide fragment of hCG is able to reduce the proliferative activity of the MCF-10F cells as well. In fact, the peptide is even more efficient to diminish cell proliferation than hCG after the $8^{th}$ day of treatment. The striking overexpression of LHCGR by MCF-10F cells when exposed to hCG or to the peptide reflects the early events that lead to intracellular changes that modify CXCR1 expression and eventually its molecular function. Also, LHCGR expression seems to be related to the tumor grade of differentiation, since the receptor is more expressed as the smaller a tumor is (22) and its expression is totally abrogated when these cells undergo through a neoplastic transformation induced by 17 β-estradiol (results not shown). Both hCG and the peptide induce a decrease of CXCR1 expression in a population of normal human mammary cells, which lead us to two important considerations. The first one is that probably this CXCR1 expression decreases as a result of a reduction of the stem cells population, and second is that down-regulation of CXCR1 could be driving a higher number of cells to apoptosis by activation of the FAK/AKT/FOXO3A pathway as it occurs when this receptor is blocked (4). Previous results from our laboratory confirm that hCG and peptide are able to decrease the FAK and AKT meanwhile they up-regulate FOXO3A expression (unpublished data).

Our data suggests that the expression of two out of the three membrane receptors assessed herein can be associated with the presence of a breast stem cell (BSC) protective phenotype, against cancer development that is evoked by hCG and peptide treatment (28-30). According to the observations of Russo and co-workers (2006a) (28) during the differentiation of the breast either during pregnancy or under the effect of exogenous hCG there is a progressive decrease in the percentage of proliferating cells and a reduction in the susceptibility of cell transformation by carcinogens (28-30). Therefore it appears that CXCR1 is related to BSC (4, 31, 32), and the increase of LHCGR mRNA seems to respond to the decrease of CXCR1 expression these genes probably act synergistically to reduce the amount of BSC in the mammary gland.

The data presented herein clearly indicate that the parous breast has a specific genomic signature that is the result of chromatin remodeling. This signature is also detected in women receiving r-hCG as well as in in vitro and in vivo experimental models. An important discovery is the finding that synthetic 15 aa peptides interact with the hCG receptor in human breast epithelial cells and also increase cell differentiation, as measured in a ductulogenic assay in collagen matrix. These peptides also abrogate cell transformation and inhibit invasiveness. These phenotypes are the result of chromatin remodeling generating a genomic signature similar than the induced by parity and r-hCG treatment.

It is anticipated that the treatment of the cells under investigation with hCG and the synthetic peptides described will be effective to reverse the process of cell transformation by increasing their ductulogenesis capacity, inhibit the invasive capacity and inhibit tumorigenesis in SCID mice. These data should provide proof that these compounds will be able to prevent and even reverse the carcinogenic phenotype. The vis-à-vis comparison of the phenotypic, genotypic and epigenetic effects of hCG and and the synthetic peptides of the invention in human breast epithelial cells at different stages of malignancy and cancer progressionl provide significant clinical information for the prevention of the transformation event and also provides insight as to means for abrogation of advanced stages of cancer, including invasion and tumorigenesis.

REFERENCES

1—Todaro M, Alea M P, Di Stefano A B, Cammareri P, Vermeulen L, Iovino F, Tripodo C, Russo A, Gulotta G, Medema J P, Stassi G. Colon cancer stem cells dictate tumor growth and resist cell death by production of interleukin-4. Cell Stem Cell 2007; 1(4):389-402.
2—Dorsam, R T and Silvio Gutkind, J S. G-protein-coupled receptors and cancer. Nat Rev Cancer 2007; 7(2):79-94.
3—Waugh D J, Wilson C. The interleukin-8 pathway in cancer. Clin Cancer Res 2008; 14(21):6735-41. Review.
4—Ginestier C, Liu S, Diebel M E, Korkaya H, Luo M, Brown M, Wicinski J, Cabaud O, Charafe-Jauffret E, Birnbaum D, Guan J L, Dontu G, Wicha M S. CXCR1 blockade selectively targets human breast cancer stem cells in vitro and in xenografts. J Clin Invest 2010; 120(2):485-97.
5—Charafe-Jauffret E, Ginestier C, Iovino F, Wicinski J, Cervera N, Finetti P, Hur M H, Diebel M E, Monville F, Dutcher J, Brown M, Viens P, Xerri L, Bertucci F, Stassi G, Dontu G, Birnbaum D, Wicha M S. Breast cancer cell lines contain functional cancer stem cells with metastatic capacity and a distinct molecular signature. Cancer Res 2009; 69(4):1302-13.
6—Russo J, Fernandez S V, Russo P A, Fernbaugh R, Sheriff F, Lareef H M, Garber J, Russo I. 1-beta-estradiol induces transformation and tumorigenesis in human breast epithelial cells. The FASEB J 20: 1622, 2006.
7—Huang y, Fernandez S V, Goodwin S, Russo P A, Russo I H, Sutter J R, Russo J. Epithelial to mesenchymal transition in human breast epithelial cells transformed by 17-β-estradiol. Cancer Res 67:11147, 2007.
8—Kocdor H, Kocdor M A, Russo J, Snider K E, Vanegas J E, Russo I H, Fernandez S V. Human chorionic gonadotropin (hCG) prevents the transformed phenotypes induced by 17 beta-estradiol in human breast epithelial cells. Cell Biol Int 2009; 33(11):1135-43.
9—Russo J, Russo I H. The etiopathogenesis of breast cancer prevention. Cancer Lett 1995; 90:81-9
10—Srivastava P, Russo J, Russo I H. Inhibition of rat mammary tumorigenesis by human chorionic gonadotropin associated with increased expression of inhibin. Mol Carcinog 1999; 26:10-9.
11—Loosfelt H, Misrahi M, Atger M, Salesse R, Thi M T V H, Jolivet A, Guiochon-Mantel A, Sar S, Jallal B, Gamier J and Milgrom E. Cloning and sequencing of porcine LH-hCG receptor cDNA: variants lackingtran smembrane domain. Science 1989; 245:525-8.
12—McFarland K C, Sprengel R, Phillips H S, Kohler M, Rosemblit N, Nikolics K, Segaloff D L, and Seeburg P H. Lutropin-choriogonadotropin receptor: an unusual member of the G protein-coupled receptor family. Science 1989; 245:494-9.
13—Russo I H, Russo J. Hormonal approach to breast cancer prevention. J Cell Biochem 2000; Suppl 34: 1-6.
14—Rao, C V. Does full-term pregnancy at a young age protect women against breast cancer through hCG? Obstet Gynecol 2000; 96: 783-786.
15—Morbeck D E, Roche P C, Keutmann H T, McCormick D J. A receptor binding site identified ip the region 81-95 of the β-subunit of human Luteinizing hormone f LHf and chorionic gonadotropin (hCG). *Mol Cell Endocrinol* 1993; 97(1-2):173-81.
16—Hu Y L, Lei Z M, Huang Z H, Rao C V. Determinants of transcription of the chorionic gonadotropin/luteinizing hormone receptor gene in human breast cells. Breast J 1999; 5:186-93.
17—Lojun S, Bao S, Lei Z M, Rao C V. Presence of functional Luteinizing hormone/chorionic gonadotropin (hCG) receptors in human breast cell lines: implications supporting the premise that hCG protects women against breast cancer. Biol Reprod 1997; 57:1202-10.
18—Meduri G, Charnaux N, Loosfelt H, et al. Luteinizing-hormone/human chorionic gonadotropin receptors in breast cancer. Cancer Res 1997; 57: 857-64.
19—Meduri G, Charnaux N, Spyratos F, Hacene K, Loosfelt H, Milgrom E. Luteinizing hormone receptor status and clinical, pathologic, and prognostic features in patients with breast carcinomas. Cancer 2003; 97: 1810-6.
20—Span P N, Manders P, Heuvel J J, et al. Molecular beacon reverse transcription-PCR of human chorionic gonadotropin-h-3, -5, and -8 mRNAs has prognostic value in breast cancer. Clin Chem 2003; 49:1074-80.
21—Taback B, Chan A D, Kuo C T, Bostick P J, Wang H J, Giuliano A E, and Hoon D S B. Detection of occult metastatic breast cancer cells in blood by a multimolecular marker assay: correlation with clinical stage of disease. Cancer Res 2001; 61:8845-50.

22—Kuijper T M, Ruigrok-Ritstier K, Verhoef-Post M, Piersma D, Bruysters M W, Berns E M, Themmen A P. LH receptor gene expression is essentially absent in breast tumor tissue: Implications for treatment. Mol Cell Endocrinol 2009; 302(1):58-64.
23—Janssens J P, Russo J, Russo I H, Michiels L, Donders G, Verjans M, Riphagen I, Bossche T V, Deleu M and Sieprath P. Human chorionic gonadotropin (hCG) and prevention of breast cancer. Mol Cell Endocrinol 2007; 269: 93-8.14. Rao C V. Does full-term pregnancy at a young age protect women against breast cancer through hCG? Obstet Gynecol 2000; 96:783-6.
24—Correa S A, Pacheco N A, Costa-Neto C M, Oliveira L, Pesquero J B, Han S W, Paiva A C, Shimuta S I. Angiotensin II AT1 receptor mutants expressed in CHO cells caused morphological change and inhibition of cell growth. Regul Pept 2005; 131(1-3):18-22.
25—Schmittgen T D, Livak K J, Analyzing real-time PCR data by the comparative CT method Nature Protocols 2008; 3,-1101-1108.
26—MacMahon B. Epidemiology and the causes of breast cancer. Int J Cancer 2006; 118: 2373-2378.
27—Alvarado M V, Russo J, Russo I H. Immunolocalization of inhibin in the mammary gland of rats treated with hCG. J Histochem Cytochem 1993; 41(1):29-34.
28—Russo J, Russo I H. Toward a physiological approach to breast cancer prevention. Cancer Epidemiol Biomarkers Prey 1994; 3(4):353e64.
29—Balogh G A, Heulings R, Mailo D A, Russo P A, Sheriff F, Russo I H, Moral R, Russo J. Genomic signature induced by pregnancy in the human breast. Int J Oncol 2006; 28(2): 399e410.
30—Russo J, Balogh G A, Chen J, Fernandez S V, Fernbaugh R, Heulings R, Mailo D A, Moral R, Russo P A, Sheriff F, Vanegas J E, Wang R and Russo I H. The concept of stem cell in the mammary gland and its implication in morphogenesis, cancer and prevention. Front Biosci 2006a; 11:151e72.
31—Iles R K, Delves P J, Butler S A. Mol Cell Endocrinol. Does hCG or hCGfβ play a role in cancer cell biology? 2010; 329(1-2):62-70.
32—Liu Q, Li J G, Zheng X Y, Jin F, Dong H T. Expression of CD133, PAX2, ESA, and GPR30 in invasive ductal breast carcinomas. Chin Med J 2009; 122(22):2763-9.

While certain of the preferred embodiments of the present invention have been described and specifically exemplified above, it is not intended that the invention be limited to such embodiments. Various modifications may be made thereto without departing from the scope of the present invention, as set forth in the following claims.

What is claimed is:

1. A method of inhibiting the initiation of breast cancer in a subject, said method comprising providing the subject with repeated administrations of an oligopeptide selected from the group consisting of SEQ ID NO: 1, SEQ ID NO: 2, SEQ ID NO: 4, variants thereof, and acceptable salts thereof,
   wherein said variant has at least 90% identity with SEQ ID NO: 1, SEQ ID NO: 2, or SEQ ID NO: 4, and
   wherein each repeated administration comprises a dose of at least 0.250 mg peptide/kg bodyweight of the subject.

2. The method of claim 1, wherein said oligopeptide administration induces genomic changes in breast tissue, said genomic changes being associated with a reduced risk for breast cancer.

3. The method according to claim 1, wherein the repeated administrations comprises three administrations per week for three months.

4. The method of claim 1, wherein said administration is selected from the group consisting of oral administration, transdermal administration, administration via a controlled release pump, parenteral or systemic administration and sublingual administration.

5. The method of claim 1, wherein said oligopeptide is SEQ ID NO: 1.

6. The method of claim 1, wherein said oligopeptide is SEQ ID NO: 2.

7. The method of claim 1, wherein said subject has a condition selected from the group consisting of the presence of mutations in the subject associated with cancer, exposure to radiation or carcinogens and previous diagnosis of cancer.

8. The method of claim 7, wherein said mutation is a BRCA1 or BRAC2 mutation.

9. A composition comprising a peptide having at least 90% identity with SEQ ID NO: 1 and a pharmaceutically acceptable carrier.

10. The composition of claim 9, wherein said peptide is disposed within a liposome.

11. The composition of claim 9, wherein said composition is within a transdermal patch.

12. The composition of claim 9, wherein said composition is a liquid.

13. The composition of claim 9, wherein said peptide has at least 95% identity with SEQ ID NO: 1.

14. The composition of claim 9, wherein said peptide is SEQ ID NO: 1.

15. The method of claim 1, wherein said variant has at least 95% identity with SEQ ID NO: 1.

16. The method of claim 1, wherein said oligopeptide is selected from the group consisting of SEQ ID NO: 1, SEQ ID NO: 2, and SEQ ID NO: 4.

* * * * *

SEQUENCE LISTING

```
<160> NUMBER OF SEQ ID NOS: 5

<210> SEQ ID NO 1
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 1

Ala Leu Cys Arg Arg Ser Thr Thr Asp Cys Gly Gly Pro Lys Asp His
1               5                   10                  15

Pro Leu Thr Ser
            20

<210> SEQ ID NO 2
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 2

Ser Tyr Ala Val Ala Leu Ser Cys Gln Cys Ala Leu Cys Arg Arg
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 3

Ser Leu Glu Pro Leu Arg Pro Arg Cys Arg Pro Ile Asn Ala Thr
1               5                   10                  15

<210> SEQ ID NO 4
<211> LENGTH: 15
```

```
<212> TYPE: PRT
<213> ORGANISM: Artificial Sequence
<220> FEATURE:
<223> OTHER INFORMATION: Synthetic Sequence

<400> SEQUENCE: 4

Ser Tyr Ala Val Ala Leu Ser Ala Gln Cys Ala Leu Cys Arg Arg
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 5

Ser Phe Pro Val Ala Leu Ser Cys Arg Cys Gly Pro Cys Arg Arg
1               5                   10                  15
```